United States Patent [19]

Chu

[11] 4,001,346

[45] Jan. 4, 1977

[54] SELECTIVE PRODUCTION OF PARA-XYLENE

[75] Inventor: Chin-Chiun Chu, South Plainfield, N.J.

[73] Assignee: Mobil Oil Corporation, New York, N.Y.

[22] Filed: Apr. 2, 1976

[21] Appl. No.: 673,167

Related U.S. Application Data

[63] Continuation-in-part of Ser. No. 538,664, Jan. 6, 1975.

[52] U.S. Cl. .................. 260/671 M; 260/671 R; 260/671 C
[51] Int. Cl.² .................. C07C 3/52; C07C 15/08
[58] Field of Search ...... 260/671 M, 671 R, 671 C; 208/DIG. 2

[56] References Cited

UNITED STATES PATENTS

| | | | |
|---|---|---|---|
| 3,394,075 | 7/1968 | Smith | 208/DIG. 2 |
| 3,437,587 | 4/1969 | Ellert et al. | 208/DIG. 2 |
| 3,489,675 | 1/1970 | Scott | 208/DIG. 2 |
| 3,669,903 | 6/1972 | Bourguet et al. | 260/671 |
| 3,728,408 | 4/1973 | Tobias | 260/671 |
| 3,751,506 | 8/1973 | Burress | 260/671 |
| 3,755,483 | 8/1973 | Burress | 260/671 |

*Primary Examiner*—Delbert E. Gantz
*Assistant Examiner*—C. E. Spresser
*Attorney, Agent, or Firm*—Charles A. Huggett; Raymond W. Barclay

[57] ABSTRACT

Process for the selective production of para-xylene by methylation of toluene in the presence of a catalyst comprising a crystalline aluminosilicate zeolite, said zeolite having a silica to alumina ratio of at least 12 and a constraint index, as hereinafter defined, within the approximate range of from 1 to 12, which catalyst has undergone prior treatment to deposit a coating of between about 15 and about 75 weight percent of coke thereon.

10 Claims, No Drawings

SELECTIVE PRODUCTION OF PARA-XYLENE

CROSS-REFERENCE TO RELATED APPLICATION

This application is a continuation-in-part of application Ser. No. 538,664 filed Jan. 6, 1975.

BACKGROUND OF THE INVENTION

1. Field of the Invention.

This invention relates to a process for the selective production of para-xylene by catalytic methylation of toluene in the presence of a precoked crystalline aluminosilicate catalyst.

2. Description of the Prior Art.

Alkylation of aromatic hydrocarbons utilizing crystalline aluminosilicate catalysts has heretofore been described. U.S. Pat. No. 2,904,607 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes alkylation of aromatic hydrocarbons in the presence of X- or Y-type crystalline aluminosilicate zeolites, specifically such type zeolites wherein the cation is rare earth and/or hydrogen. U.S. Pat. No. 3,751,504 to Keown et al. and U.S. Pat. No. 3,751,506 to Burress describe vapor phase alkylation of aromatic hydrocarbons with olefins, e.g. benzene with ethylene, in the presence of a ZSM-5 type zeolite catalyst.

The alkylation of toluene with methanol in the presence of a cation exchanged zeolite Y has been described by Yashima et al. in the Journal of Catalysis 16, 273–280 (1970). These workers reported selective production of para-xylene over the approximate temperature range of 200° to 275° C., with the maximum yield of para-xylene in the mixture of xylenes, i.e. about 50 percent of the xylene product mixture, being observed at 225° C. Higher temperatures, were reported to result in an increase in the yield of meta-xylene and a decrease in production of para and ortho-xylenes.

While the above-noted prior art is considered of interest in connection with the subject matter of the present invention, the methylation process described herein utilizing a catalyst of a crystalline aluminosilicate zeolite having a silica/alumina ratio of at least about 12, a constraint index of from 1 to 12 and which has undergone precoking to achieve unexpectedly high selective production of para-xylene has not, insofar as is known, been heretofore described.

Of the xylene isomers, i.e. ortho-, meta- and para-xylene, the latter is of particular value being useful in the manufacture of terephthalic acid which is an intermediate in the manufacture of synthetic fibers such as "Dacron". Mixtures of xylene isomers either alone or in further admixture with ethylbenzene, generally containing a concentration of about 24 weight percent para-xylene in the equilibrium mixture, have been previously separated by expensive superfraction and multistage refrigeration steps. Such process, as will be realized, has involved high operation costs and has a limited yield.

SUMMARY OF THE INVENTION

In accordance with the present invention, there has been discovered a process for selectively producing para-xylene in preference to meta- or ortho-xylene by reaction of toluene with a methylating agent in the presence of a catalyst comprising a crystalline aluminosilicate zeolite, said zeolite having a silica to alumina ratio of at least about 12 and a constraint index within the approximate range of from 1 to 12, which catalyst has undergone prior treatment to deposit a coating of between about 15 and about 75 weight percent of coke thereon.

Compared to a conventional thermodynamic equilibrium xylene mixture in which the para:meta:ortho is approximately 1:2:1, the process described herein affords a xylene product having a para:meta:ortho ratio of about 3:2:1 or higher. The improved para-xylene yield reduces the cost of separation of para-xylene from its isomer which is the most expensive step in the current method employed for producing para-xylene.

The present process comprises methylation of toluene preferably by reaction of the latter with methanol in the presence of a particular modified crystalline aluminosilicate catalyst. The catalyst employed contains a crystalline aluminosilicate zeolite having a silica to alumina ratio of at least about 12 and a constraint index of from about 1 to about 12, which has been modified by the deposition thereon of a carbonaceous coating commonly referred to as "coke" resulting from the decomposition of hydrocarbons, generally under conditions of high temperature, in the presence of the specified catalyst. Generally, precoking of the catalyst will be accomplished by initially utilizing the uncoked catalyst in the reaction of interest, i.e. methylation of toluene, during which coke is deposited on the catalyst surface and thereafter controlled within the above-noted range of about 15 to about 75 weight percent by periodic regeneration by exposure to an oxygencontaining atmosphere at an elevated temperature.

Indeed, one advantage of utilizing the catalyst described herein is its ease of regenerability. Thus, after use of the precoked catalyst for effecting the desired mthylation reaction for a period of time such that the activity of the catalyst declines to a point where further use becomes uneconomical, it can be readily regenerated by burning off excess coke in an oxygen-containing atmosphere, e.g. air, at a temperature, generally within the approximate range of 400° to 700° C. The catalyst may thereby be rendered substantially free of coke, necessitating subjecting the catalyst to a precoking step. Alternatively, the catalyst may be partially freed of coke during the combustion regeneration step to leave a residual deposition of coke on the surface of the catalyst, the amount of which is within the approximate range of 15 to 75 weight percent coke. The thus regenerated catalyst can then be employed for further use in achieving the desired selective production of para-xylene.

The zeolite catalysts herein described are members of a novel class of zeolites exhibiting some unusual properties. These catalysts induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type.

Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratios of at least about 30. Such catalysts, after activation, acquire an intracrystalline sorption capacity for normal hexane which is greater than that for water, i.e. they exhibit "hydrophobic" properties. It is believed that this hydrophobic character is advantageous in the present invention.

The type zeolites usefuul in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1,000° F. for at least 15 minutes. The catalyst is then flushed with helium and the temperature adjusted between 550° and 950° F. to give an overall conversion between 10 and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts are:

| CAS | C.I. |
| --- | --- |
| ZSM-5 | 8.3 |
| ZSM-11 | 8.7 |
| ZSM-12 | 2 |
| ZSM-21 | 4.5 |
| ZSM-35 | 4.5 |
| TMA Offretite | 3.7 |
| Beta | 0.6 |
| ZSM-4 | 0.5 |
| H-Zeolon | 0.5 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° to 950° F., with accompanying conversion between 10 and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F. to 950° F., the constraint index will have a value for any given zeolite of interest herein within the approximate range of 1 to 12.

The class of zeolites defined herein is exemplified by ZSM-5, ZSM-11, ZSM-12, ZSM-21, ZSM-35 and other similar materials. Recently issued U.S. Pat. No. 3,702,886 describing and claiming ZSM-5 is incorporated herein be reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-21 is more particularly described in U.S. Pat. application Ser. No. 560,412, filed Mar. 20, 1975. This zeolite can be identified, in terms of mole ratios of oxides and in anhydrous state, as follows:

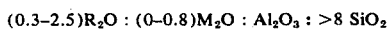
$$(0.3-2.5)R_2O : (0-0.8)M_2O : Al_2O_3 : >8\ SiO_2$$

wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

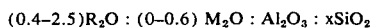
$$(0.4-2.5)R_2O : (0-0.6)\ M_2O : Al_2O_3 : xSiO_2$$

wherein R is an organic nitrogen-containing cation derived from a 2-(hydroxyalkyl)trialkylammonium compound, wherein alkyl is methyl, ethyl or a combination thereof, M is an alkali metal, especially sodium, and x is from greater than 8 to about 50.

The synthetic ZSM-21 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33A.

TABLE I

| d(A) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-21 is its sorptive capacity providing said zeolite to have increased capacity for 2-methylpentane (with respect to n-hexane sorption by the ratio n-hexane/2-methyl-pentane) when compared with a hydrogen from of natural ferrierite resulting from calcination of an ammonium exchanged form. The characteristic sorption ratio n-hexane/2-methylpentane for ZSM-21 (after calcination at 600° C.) is less than 10, whereas that ratio for the natural ferrierite is substantially greater than 10, for example, as high as 34 or higher.

Zeolite ZSM-21 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH⁻/SiO₂ | 0.05–0.5 | 0.07–0.49 |
| H₂O/OH⁻ | 41–500 | 100–250 |
| SiO₂/Al₂O₃ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90° to about 400° c. for a period of time of from about 6 hours to about 100 days. A more preferred temperature range is from about 150° to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

ZSM-35 is more particularly described in U.S. Pat. application Ser. No. 528,061, filed Nov. 29, 1974. This zeolite can be identified, in terms of mole ratios of oxides and in the anhydrous state, as follows:

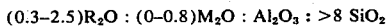
$$(0.3-2.5)R_2O : (0-0.8)M_2O : Al_2O_3 : >8\ SiO_2$$

wherein R is an organic nitrogen-containing cation derived from ethylenediamine or pyrrolidine and M is an alkali metal cation, and is characterized by a specified X-ray powder diffraction pattern.

In a preferred synthesized form, the zeolite has a formula, in terms of mole ratios of oxides and in the anhydrous state, as follows:

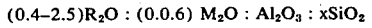
$$(0.4-2.5)R_2O : (0.0.6)\ M_2O : Al_2O_3 : xSiO_2$$

wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5A. This very weak line, however, is determined not to be a significant line for ZSM-35.

TABLE II

| d(A) | I/Io |
|---|---|
| 9.6 ± 0.20 | Very Strong - Very Very Strong |

TABLE II-continued

| d(A) | I/Io |
|---|---|
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/ 2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH⁻/SiO₂ | 0.05–0.5 | 0.07–0.49 |
| H₂O/OH⁻ | 41–500 | 100–250 |
| SiO₂/Al₂O₃ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90° to about 400° C. for a period of time of from about 6 hours to about 100 days. A more preferred temperature range is from about 150° to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1,000° F. for one hour, for example, followed by base exchange with ammonium salts followed by calcination at 1,000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1,000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12, ZSM-21 and ZSM-35, with ZSM-5 particularly preferred.

The catalysts of this invention may be in the hydrogen form or they may be base exchanged or impregnated to contain ammonium or a metal cation complement. It is desirable to calcine the catalyst after base exchange. The metal cations that may be present include any of the cations of the metals of Groups I through VIII of the periodic table. However, in the case of Group IA metals, the cation content should in no case be so large as to effectively inactivate the catalyst.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1,000 cubic Angstroms, as given, e.g., on page 19 of the article on Zeolite Structure by W. M. Meir. This paper, the entire contents of which are incorporated herein by reference, is included in "Proceedings of the Conference on Molecular Seives, London, Apr. 1967, " published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures.

This free space, however, is important as the locus of catalytic activity.

Crystal framework densities of some typical zeolites are:

| Zeolite | Void Volume | | Framework Density | |
|---|---|---|---|---|
| Ferrierite | 0.28 | cc/cc | 1.76 | g/cc |
| Mordenite | .28 | | 1.7 | |
| ZSM-5, -11 | .29 | | 1.79 | |
| Dachiardite | .32 | | 1.72 | |
| L | .32 | | 1.61 | |
| Clinoptilolite | .34 | | 1.71 | |
| Laumontite | .34 | | 1.77 | |
| ZSM-4 (Omega) | .38 | | 1.65 | |
| Heulandite | .39 | | 1.69 | |
| P | .41 | | 1.57 | |
| Offretite | .40 | | 1.55 | |
| Levynite | .40 | | 1.54 | |
| Erionite | .35 | | 1.51 | |
| Gmelinite | .44 | | 1.46 | |
| Chabazite | .47 | | 1.45 | |
| A | .5 | | 1.3 | |
| Y | .48 | | 1.27 | |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table indlucing, by way of example, nickel, zinc, calcium or rare earth metals.

The crystals of zeolite in a form substantially free of alkali metal, i.e. containing less than about 1.5 weight percent alkali metal, are then subjected to the above-described precoking treatment.

The process of this invention may be carried out as a batch-type, semi-continuous or continuous operation utilizing a fixed or moving bed catalyst system. Multiple injection of the methylating agent, e.g. methanol, may suitably be employed. A preferred embodiment entails use of a fluidized catalyst zone wherein the reactants, i.e. toluene and methylating agent, are passed concurrently or countercurrently through a moving fluidized bed of the catalyst. The fluidized catalyst after use is conducted to a regeneration zone wherein coke is burned from the catalyst preferably to an extent such that residual coke remaining on the catalyst is between about 15 and about 75 weight percent, after which the regenerated catalyst is recycled to the conversion zone for further contact with the toluene and methylating agent reactants.

In practicing the desired methylation process it may be desirable to incorporate the modified zeolite in another material resistant to the temperatures and other conditions employed in the methylation process. Such matrix materials include synthetic or naturally occurring substances as well as inorganic materials such as clay, silica and/or metal oxides. The latter may be either naturally occurring or in he form of gelatinous precipitates or gels including mixtures of silica and metal oxides. Naturally occurring clays which can be composited with the modified zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the modified zeolites employed herein may be composited with a porous matrix material, such as silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of finely divided modified zeolite and inorganic oxide gel matrix may vary widely with the zeolite content ranging from between about 1 to about 99 percent by weight and more usually in the range of about 5 to about 80 percent by weight of the composite. A particularly suitable combination is one containing about 65 weight percent of the zeolite in about 35 weight percent of a relatively inactive alumina matrix.

The amount of coke deposited on the catalyst is within the approximate range of 15 to 75 weight percent. Generally in order to achieve the same para-xylene/total xylenes ratio, a higher coke content is required for extrudate catalyst or catalyst wherein the crystalline aluminosilicate zeolite is admixed with a binder or matrix than when the pure crystalline aluminosilicate zeolite is employed. Preferably, the amount of coke deposited on the catalyst surface will be between about 20 and about 75 weight percent.

Methylation of toluene in the presence of the above-described catalyst is effected by contact of the toluene with a methylating agent, preferably methanol, at a temperature between about 300° and about 750° C and preferably between about 400° and about 700° C. At the higher temperatures, the zeolites of high silica/alumina ratio are preferred. For example, ZSM-5 of 300 $SiO_2/Al_2O_3$ ratio and upwards is very stable at high temperatures. The reaction generally takes place at atmospheric pressure, but the pressure may be within the approximate range of 1 atmosphere to 1,000 psig. A weight hourly space velocity of between about 1 and about 2000 is employed. The molar ratio of methylating agent to toluene is generally between about 0.05 and about 5. When methanol is employed as the methylating agent a suitable molar ratio of methanol to toluene has been found to be approximately 0.1 to 8 moles of methanol per mole of toluene. With the use of other methylating agents, such as methylchloride, methylbromide, dimethylether or dimethylsulfide, the molar ratio of methylating agent to toluene may vary within the aforenoted range. Reaction is suitably accomplished utilizing a weight hourly space velocity of between about 1 and about 2000 and preferably between about 5 and about 1,500 weight of charge per weight of catalyst per hour. The reaction product consisting predominantly of para-xylene, together with comparatively smaller amounts of meta-xylene and ortho-xylene may be separated by any suitable means, such as by passing the same through a water condenser and subsequently passing the organic phase through a column in which chromatographic separation of the xylene isomers is accomplished.

The following examples will serve to illustrate the process of this invention without limiting the same:

EXAMPLE 1

ZSM-5 crystals were obtained using the following reactants:

| Silicate Solution | |
|---|---|
| 42.2 lb. | Q-Brand Sodium Silicate ($Na_2O/SiO_2 = 3.3$) |
| 52.8 lb. | Water |
| Acid Solution | |
| 612 grams | Aluminum Sulfate |
| 1600 grams | Sulfuric Acid |
| 7190 grams | Sodium Chloride |
| 72.2 lb. | Water |
| Organics | |
| 1290 grams | Tri-n-propylamine |
| 1110 grams | n-Propylbromide |

The silicate solution and acid solution were nozzle mixed to form a gelatinous precipitate that was charged to a 30 gallon stirred autoclave. When gelation was complete the organics were added and the temperature raised to 315° F. with agitation. The reaction mixture was held at 315° F. with an agitation rate of 121 RPM for 17 hours. The product at this time was analyzed by X-ray diffraction and was reported to be ZSM-5. The product was then washed free of soluble salts and dried. Analysis of the product gave the following in terms of mole ratios:

| | |
|---|---|
| $Al_2O_3$ | 1.0 |
| $SiO_2$ | 74.4 |
| $Na_2O$ | 0.31 |
| N | 2.26 |
| C | 21.9 |

The ZSM-5 so prepared was precalcined in air at 370° C and thereafter ammonium exchanged by contacting twice with 5N $NH_4Cl$ solution at 100° C (15 ml per gram zeolite), once for 16 hours, the second time for 4 hours, filtered, washed free of chloride and air dried.

The resulting ammonium form of ZSM-5 was converted to the hydrogen form by calcination in air at 1° C/minute to 538° and then held at 538° C for 10 hours.

A mixture of toluene (1715 grams) and methanol (426 grams) in a molar ratio of 1.4/1 was passed over 5 grams of the so prepared HZSM-5 at 550° C and a weight hourly space velocity of 5 weight of charge/weight of catalyst/hour for a total of 85 hours. Activity of the catalyst decreased from initial conversion of toluene at 70 weight percent to nil at the end of 85 hours. The weight of catalyst was increased by 77 percent, due to coking.

A portion of the coked catalyst was regenerated in air at 550° C overnight. Alkylation of toluene with methanol was carried out by passing a 1.4:1 molar ratio mixture of toluene and methanol over 0.8 grams of the regenerated catalyst containing about 30 weight percent coke at a temperature of 490° C and a weight hourly space velocity of 11.5 weight of charge per weight of catalyst/hour. Toluene conversion was 60 percent and the para/meta/ortho ratio in the xylene product was 50/33/17.

EXAMPLE 2

After use in the process of Example 1, the catalyst was regenerated in air at 550° C for 16 hours. Alkylation of toluene with methanol was carried out by passing a 1.4:1 molar ratio mixture of toluene and methanol over 0.8 grams of the regenerated catalyst containing about 30 weight percent coke at a temperature of 490° C and a weight hourly space velocity of 18 weight of charge/weight of catalyst/hour. Toluene conversion was 49 percent and the para/meta/ortho ratio was 51/32/16.

EXAMPLE 3

A catalyst was prepared by blending 5 weight percent HZSM-5 and 95 weight percent silica gel.

Toluene and methanol in a 1:1 molar ratio were passed over this catalyst at a temperature of 550° C at a weight hourly space velocity of 250. Methanol conversion was 11 weight percent. The xylene content in the aromatics products amounted to 50 weight percent. After 32.5 hours on stream, the catalyst had deactivated considerably due to the accumulation of coke thereon and produced 100 percent selectivity to paraxylene at about 1 percent toluene conversion.

EXAMPLE 4

A catalyst was prepared by blending 5 weight percent HZSM-5 extrudate (containing 65 wt. percent HZSM-5 and 35 wt. percent $Al_2O_3$ binder) and 95 weight percent silica gel.

Toluene and methanol in a 1:1 molar ratio were passed over this catalyst at a temperature of 550° C at a weight hourly space velocity of 241. Methanol conversion was 10 weight percent. The xylene content in the aromatics product was 100 weight percent. After 4.5 hours on stream the catalyst had deactivated considerably due to the accumulation of coke thereon and gave 100 percent selectivity to para-xylene at about 1 percent toluene conversion.

EXAMPLE 5

Over a fixed bed of extrudate catalyst containing 35 weight percent alumina and 65 weight percent HZSM-5, prepared as in Example 1 of U.S. Pat. No. 3,751,506, a feed of toluene was contacted with methyl alcohol in the mole ratio of toluene to methyl alcohol of 2:1. The reactor inlet temperature was 870° F. and the reactor pressure was maintained at atmosphere. The total feed weight hourly space velocity was 4. The composition of the liquid product was as follows:

| Component | Wt. percent Total product |
|---|---|
| Toluene | 59.6 |
| Xylenes | 29.7 |
| Para/Total Xylenes | 24.5 |
| Meta/Total Xylenes | 52.6 |
| Ortho/Total Xylenes | 22.9 |
| Benzene | 3.2 |
| $C_9$ | 6.2 |
| $C_9^+$ | 1.1 |
| Others | .2 |
| Percent Coke on Catalyst After the Run | 3.6 |

It will be evident from the results that the amount of coke deposited on he catalyst, i.e. 3.6 weight percent, was insufficient to afford selective production of para-xylene, since the para/meta/ortho xylene concentration was essentially that of the equilibrium mixture.

Examples 6–8

An extrudate catalyst similar to that used in Example 5 was pre-coked prior to alkylation. The reaction feed and conditions were the same as in the preceding example. The composition of the liquid product was as follows:

| Example | 6 | 7 | 8 |
|---|---|---|---|
| Percent Coke on Catalyst | 30 | 26 | 27 |
| Toluene | 72.9 | 72.4 | 72.8 |
| Xylenes | 20.7 | 20.6 | 19.8 |
| Para/Total Xylenes | 37.8 | 30.0 | 30.7 |
| Meta/Total Xylenes | 42.3 | 48.6 | 48.1 |
| Ortho/Total Xylenes | 19.9 | 21.4 | 21.2 |
| Benzene | .2 | .5 | .4 |
| $C_9$ | 5.6 | 5.9 | 6.4 |
| $C_9^+$ | .5 | .5 | .5 |
| Others | .1 | .1 | .1 |

From the above results, it will be seen that with deposition of coke on the catalyst in the range of para-xylene produced was greater than that present in the equilibrium mixture, 1.0 para-xylene was selectively produced.

EXAMPLES 9–17

An HZSM-5 catalyst prepared as in Example 1 was employed for methylation of toluene using a 2:1 mole ratio of toluene to methyl alcohol. The reactor inlet temperature was 870° F., the pressure was atmospheric and the weight hourly space velocity was 4. The catalyst used in Example 9 was not pre-coked, while the catalysts used in the remaining examples were pre-coked to deposit various amounts of coke on the catalyst as indicated. The composition of the liquid products obtained in each instance are shown below:

| Example | 9 | 10 | 11 | 12 | 13 | 14 | 15** | 16** | 17** |
|---|---|---|---|---|---|---|---|---|---|
| Percent Coke on Catalyst | 3.0* | 8.1 | 15 | 16 | 20 | 23 | 23 | 27 | 24 |
| Liquid Products | | | | | | | | | |
| Benzene | 4.2 | .7 | .5 | .5 | .4 | .4 | .3 | .3 | .3 |
| Toluene | 60.5 | 70.0 | 71.7 | 73.2 | 75.9 | 80.1 | 72.2 | 74.1 | 74.0 |
| Xylenes | 28.2 | 21.1 | 20.3 | 19.5 | 17.0 | 14.7 | 20.6 | 19.7 | 19.4 |
| para/Total Xylenes | 24.2 | 24.3 | 24.7 | 25.0 | 33.9 | 41.2 | 27.1 | 30.9 | 32.4 |
| meta/Total Xylenes | 52.8 | 52.6 | 52.2 | 52.0 | 45.0 | 39.6 | 50.4 | 47.7 | 46.8 |
| ortho/Total Xylenes | 23.0 | 23.1 | 23.1 | 23.0 | 21.1 | 19.1 | 22.5 | 21.4 | 20.7 |
| $C_9$ | 5.6 | 7.5 | 6.5 | 6.2 | 6.2 | 4.1 | 6.2 | 5.5 | 5.8 |
| $C_9^+$ | 1.2 | .6 | .8 | .4 | .3 | .6 | .5 | .4 | .4 |
| Others | .3 | .2 | .1 | .1 | .2 | .1 | .1 | .1 | .1 |

*Percent Coke After the Run
**Catalyst Used Was ⅛" Pellets

From the above results, it will be seen that a minimum deposit of about 15 weight percent of coke on the catalyst is necessary before selective production of para-xylene is achieved. Thus, it will be evident from the results of Example 10 that even with an amount of coke deposited on the catalyst exceeding 8 weight percent, the para/meta/ortho xylene concentration was essentially that of the equilibrium mixture.

It is to be understood that the foregoing description is merely illustrative of preferred embodiments of the invention of which many variations may be made by those skilled in the art within the scope of the following claims without departing from the spirit thereof.

I claim:

1. A process for the selective production of para-xylene which comprises reacting toluene with a methylating agent in the presence of a catalyst comprising a crystalline aluminosilicate zeolite, said zeolite having a silica to alumina ratio of at least about 12 and a constraint index within the approximate range from 1 to 12, which catalyst has undergone prior treatment to deposit a coating of between about 15 and about 75 weight percent of coke thereon.

2. The process of claim 1 wherein said methylating agent is methanol, methylchloride, methylbromide, dimethylether or dimethylsulfide.

3. The process of claim 1 wherein the step of reacting toluene with a methylating agent is carried out at a temperature between about 300° and 700° C, a pressure of between about 1 atmosphere and 1,000 psig, a weight hourly space velocity between about 1 and about 2,000 employing a molar ratio of methylating agent to toluene of between about 0.05 and about 5.

4. The process of claim 1 wherein said crystalline aluminosilicate zeolite is characterized by a silica/alumina ratio in excess of 30.

5. The process of claim 1 wherein said crystalline aluminosilicate zeolite is ZSM-5.

6. The process of claim 1 wherein said methylating agent is methanol.

7. The process of claim 3 wherein said temperature is between about 400° and about 700° C.

8. The process of claim 3 wherein said weight hourly space velocity is between about 5 and about 1,500.

9. The process of claim 3 wherein said methylating agent is methanol present in an amount such that the molar ratio of methanol to toluene is approximately 0.1 to 8.

10. The process of claim 1 wherein said catalyst has undergone prior treatment to deposit a coating of about 30 weight percent of coke thereon.

* * * * *

UNITED STATES PATENT AND TRADEMARK OFFICE
CERTIFICATE OF CORRECTION

PATENT NO. : 4,001,346
DATED : January 4, 1977
INVENTOR(S) : CHIN-CHIUN CHU

It is certified that error appears in the above-identified patent and that said Letters Patent are hereby corrected as shown below:

Column 5, line 58, "from" should be --form--.

Column 12, line 7, "51/32/16" should be --52/32/16--.

Column 13, line 21, prior to "para-xylene" insert --26 to 30 weight percent, the amount of--.

Column 13, line 23, delete "1.0" and insert --i.e.--.

Signed and Sealed this

Thirty-first Day of May 1977

[SEAL]

Attest:

RUTH C. MASON
Attesting Officer

C. MARSHALL DANN
Commissioner of Patents and Trademarks